(12) United States Patent
Goldenberg

(10) Patent No.: US 7,033,572 B2
(45) Date of Patent: *Apr. 25, 2006

(54) NON-ANTIGENIC TOXIN-CONJUGATE AND FUSION PROTEIN OF INTERNALIZING RECEPTOR SYSTEM

(75) Inventor: David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 389 days.

This patent is subject to a terminal disclaimer.

(21) Appl. No.: 10/117,342

(22) Filed: Apr. 8, 2002

(65) Prior Publication Data

US 2003/0031669 A1    Feb. 13, 2003

Related U.S. Application Data

(62) Division of application No. 09/599,550, filed on Jun. 23, 2000, now Pat. No. 6,399,068, which is a division of application No. 08/949,758, filed on Oct. 14, 1997, now Pat. No. 6,083,477.

(60) Provisional application No. 60/028,430, filed on Oct. 17, 1996.

(51) Int. Cl.
    *A61M 36/14*    (2006.01)

(52) U.S. Cl. ............... 424/1.41; 424/1.11; 424/9.1; 424/85.1; 424/85.2; 424/130.1; 424/144.1; 424/184.1; 424/192.1; 514/2; 514/8; 514/12; 530/387.1; 530/387.3; 530/388.22

(58) Field of Classification Search ............... 424/1.11, 424/1.61, 9.1, 85.1, 85.2, 130.1, 144.1, 184.1, 424/192.1; 514/2, 8, 12; 530/387.1, 387.3, 530/388.22
See application file for complete search history.

(56) References Cited

U.S. PATENT DOCUMENTS

| 4,837,003 A | 6/1989 | Nicolotti |
| 6,083,477 A * | 7/2000 | Goldenberg ............... 424/1.41 |

FOREIGN PATENT DOCUMENTS

| WO | WO 92/00762 | 1/1992 |
| WO | WO 93/23062 | 11/1993 |
| WO | WO 94/07535 | 4/1994 |
| WO | WO 95/30695 | 11/1995 |
| WO | WO 96/26274 | 8/1996 |

OTHER PUBLICATIONS

Anderson et al., "Functional characterization of the Human Interleukin-15 Receptor α Chain and Close Linkage of IL5RA and IL2RA Genes", The Journal of Biological Chemistry, vol. 270(50), pp. 29862-29868, (1995).

de Jong et al., "Interaction of IL-15 with the Shared IL-2 Receptor β and $γ_c$ Receptor-Ligand Complex", The American Association of Immunologists, vol. 156(4), pp. 1339-1348, (1996).

Chae et al., "Distribution of IL-15 Receptor α -Chains on Human Peripheral Blood Mononuclear Cells and Effect of Immunosuppressive Drugs on Receptor Expression", The Journal of Immunology, vol. 157(7), pp. 2813-2819, (1996).

"The Merck Manual of Diagnosis & Therapy", Burns & Berkov Published by Merck Research Labs, 17th edition (1999).

* cited by examiner

*Primary Examiner*—Prema Mertz
(74) *Attorney, Agent, or Firm*—Heller Ehrman LLP

(57) ABSTRACT

A conjugate of a toxin and a cytokine, and a fusion protein comprising a bispecific antibody that has a first specificity for a cell marker specific to a malignant cell and a second specificity for a region of IL-15α, each optionally further comprising a radionuclide, are useful therapeutic reagents for treating leukemias and lymphomas.

7 Claims, No Drawings

NON-ANTIGENIC TOXIN-CONJUGATE AND FUSION PROTEIN OF INTERNALIZING RECEPTOR SYSTEM

BACKGROUND OF THE INVENTION

The present invention relates to a fusion protein of a component of an internalizing receptor system and a moiety that binds to a specific cellular surface marker on a cell, to a conjugate of a toxin and a ligand for the internalizing receptor system, and to a method of tumor therapy using the conjugate and internalizing receptor system.

There is now a fairly large and growing body of experience in the use of monoclonal antibodies (mAbs) for the therapy of lymphoma. Several studies targeting different B-cell restricted CD (clusters of differentiation) antigens have shown promising results. These studies have used radiolabeled mAbs and, to a lesser extent, mAb-toxin conjugates, and have targeted CDs19-22, CD37, and HLA-DR.

MAbs used in lymphoma therapy differ in their ability to bind cognate antigen and to become internalized. For example, CD22 exhibits efficient internalization as well as reexpression of antigen after internalization. It suffers, however, from relatively low expression levels on most B-cell malignancies, and is not widely expressed, e.g., it is expressed on only 30–50% of cases of B-cell lymphocytic leukemia (B-CLL).

The present inventor has studied an anti-CD22 mAb, LL2. Preliminary studies using LL2 labeled with $^{131}$I for both therapy and imaging of NHL have produced response rates of 30–90+%, with varying percentages of complete responses and differences in durability of response. Higher response rates and longer disease-free survival have been associated with higher total doses of antibody and of radioactivity, which usually have required autologous bone marrow or peripheral stem cell rescue. While the results are encouraging, it is desired to increase therapeutic efficacy and decrease toxicity, particularly myelotoxicity.

The CD20 antigen, in contrast to the CD22 antigen, is a quite highly expressed B-cell restricted antigen that is expressed on a wide range of B-cell malignancies, ranging from acute lymphocytic leukemia (ALL) to the more differentiated B-Cell (B-CLL) and non-Hodgkin's lymphoma (NHL), and even to hairy cell leukemia (HCL). It generally is expressed on cells in the vast majority of cases of these malignancies at a high antigen density. A major disadvantage of CD20 is that it is a slowly internalizing antigen. For RAIT directed against CD20 this feature may not be a problem, but it militates significantly against the use of CD20 for toxin-based therapy.

A further problem of CD20 is the fact that B-cell malignancies exhibit a more rapid dissociation of bound anti-CD20 mAbs from the surface as compared to nonlymphoma tumor cells. This suggests that a therapy that uses bonding to a B-cell restricted antigen, particularly those characterized by slow internalization, would not be successful.

A variety of mAb-toxin constructs have been tested in both in vitro experiments and human trials. These studies have demonstrated potent and specific effects of these reagents. Most of the toxin molecules that have been used derive from either plant or bacterial sources and hence produce allergenic sensitization in patients. This severely limits the duration of therapy.

While major progress has been made in the therapy of B-cell malignancies such as NHL and B-CLL, there remain a substantial number of patients with B-cell malignancies who exhibit primary resistance to, or relapse after, optimal chemotherapy. A therapy that is effective over long periods of time in most or all patients with B-cell malignancies is desired.

SUMMARY OF THE INVENTION

It is therefore an object of the present invention to provide a more effective and less toxic anti-tumor therapy, particularly a therapy for treatment of B-cell malignancies, such as NHL and B-CLL.

It is another object of the invention to improve the value as antigenic targets of slowly internalizing surface antigens such as the CD20 antigen.

It is a further object of the invention to overcome the tendency of antibodies bound to the surface of lymphoma cells to dissociate rapidly from the surface of the cells.

It is yet another object of the present invention to use B-cell restricted antigens, particularly the CD20 antigen, in anti-tumor therapy.

These and other objects of the invention are achieved by providing a conjugate of toxin or therapeutic radionuclide and IL-15, and a fusion protein comprising a bispecific antibody that has a first specificity for a cell marker specific to a malignant cell and a second specificity for a region of IL-15α, each optionally further comprising a diagnostic radionuclide, which are useful therapeutic reagents for treating leukemias and lymphomas.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

It has been discovered, surprisingly, that the value of surface antigens as antigenic targets can be improved significantly by functionally linking them to a high affinity, internalizing receptor system. The present invention is of particular advantage in the case of surface antigens that do not internalize or that internalize slowly. A preferred example of a high affinity, internalizing receptor system is the IL-15 receptor system. When the IL-15 receptor system is used, it can be employed with all malignant cells that contain the $\beta/\gamma_c$ chains of IL-15 receptor. The presence of $\beta/\gamma_c$ chains of IL-15 on the cells provides the basis for a continuously internalizing receptor system that can be bridged to a surface antigen, particularly a slowly internalizing antigen, by way of a bispecific fusion protein and cognate ligand. The method according to the invention results in increased intracellular delivery into the malignant cell of cytotoxic ligands. It also improves methodologies in which a radionuclide is used as a therapeutic agent, by producing a tighter binding of the radionuclide to the malignant cell and by reducing dissociation of the targeting agent from the cell surface.

In accordance with the invention, malignant cells are pretargeted with a fusion protein. The fusion protein comprises a region of IL-15α, preferably an extracellular domain, and a bispecific antibody or antibody fragment that has a first specificity for a cell marker specific to a malignant cell marker and a second specificity for the region of IL-15α. The fusion protein is positioned on the malignant cells by means of the surface antigen expressed by the malignant cells. In an alternative embodiment, the fusion protein is formed in situ, by first administering the bispecific antibody, and then administering IL-15α which binds to the bispecific antibody that is already bound to the malignant cells. In either case, addition of an armed ligand comprising IL-15 ligand armed with a toxin or with a radionuclide then results in the formation of a trimeric complex of the $\beta/\gamma_c$ chains of IL-15 receptor, in which the α-chain of IL-15 receptor attached to the surface antigen and IL-15/toxin and/or radionuclide conjugate. Alternatively, both the fusion and the trimeric complex can be formed in situ. This leads to rapid internalization of toxin and/or radionuclide into the malignant cells. While internalization is not necessary for a therapeutic radionuclide to be effective, the trimeric complex provides a tighter binding to the malignant cells, and thus improves these modalities as well.

Receptor complexes for both IL-2 and IL-15 have three primary chains. The β and $\gamma_c$ chains are common to the two receptors, and there are individual, private alpha chains, IL-2Rα and IL-1SRα. The IL-2/IL-2 receptor system consists of at least three subunits, IL-2Rα, IL-2Rβ and IL-2R$\gamma_c$. This multi-subunit receptor is capable of binding ligand with high affinity and the ligand/receptor complex is rapidly internalized ($t_{1/2} \approx 15$ min). IL-2Rα when expressed in the absence of the other two chains internalizes slowly, and is unable to transduce a signal when expressed by itself. When IL-2Rα is juxtaposed to the other subunits by the presence of ligand the entire ligand/αβγ complex internalizes at the rapid rate intrinsic to the IL-2Rβ/$\gamma_c$ dimer. IL-2Rα thus raises the affinity of the $\beta/\gamma_c$ complex from $K_a \approx 10^9$ to $\approx 10^{11}$ $M^{-1}$.

IL-15Rα is structurally similar to IL-2Rα, and is of similar size. As compared to IL-2Rα, IL-15Rα has an affinity for its cognate ligand ($K_a \geq 10^{10}$ $M^{-1}$) that is at least two orders of magnitude greater than that of IL-2Rα for its ligand. IL-15Rα, like IL-2Rα, has a short intracytoplasmic domain and is unable to transduce a signal when expressed by itself. Thus, the IL-15/IL-15R system operates in a similar fashion to the IL-2/1L-2R system and will internalize all three of its receptor components.

The antigen to which the fusion protein containing the IL-15α is anchored is one that is specific to the malignant cell type. In a preferred embodiment, the antigen is a high-density B-cell restricted antigen. As shown herein, there is expression in malignant B-cells of the β and $\gamma_c$ chains of IL-15 receptor, and little or no expression of the receptor. The presence of $\beta/\gamma_c$ chains of IL-15 receptor on malignant B-cells forms the basis for a continuously internalizing receptor system that can be used in conjunction with B-cell restricted antigens specifically to introduce toxin, and optionally radionuclides, into malignant B-cells. This system can be self-amplifying in that internalized receptors can be either recycled or resynthesized and expressed.

For treatment of NHL, B-CLL, HCL and ALL, the high-density CD20 antigen is a particularly suitable surface antigen. For ALL or multiple myeloma, CD38 is suitable, while for acute myelogenous leukemia (AML) or chronic myelogenous leukemia (CML), the CD15 antigen can be used. In addition a variety of solid tumor surface antigens have been described, and any of these can be used in accordance with the present invention.

A bispecific antibody-based molecule, preferably a Mab, is used as the vehicle to position the α-chain of the IL-15 receptor on the surface of the targeted cells. Positioning large amounts of IL-15Rα on cells that already express the $\beta/\gamma_c$ chains of IL-15 receptor will, after addition of armed IL-15 ligand, induce internalization of this ligand/receptor complex by interaction with the β and $\gamma_c$ chains of IL-15 receptor already present on the cells.

Murine Mab frequently induce human-anti-mouse antibodies (HAMA). When such Mab are used in the present invention, this problem of immunogenicity is minimized by genetically engineering the murine Mab using either chimerization or humanization. Both strategies involve the replacement of some part of the murine sequences with human immunoglobulin sequences. In the chimeric approach the constant regions are replaced with corresponding human sequences. With humanization there is additional replacement of framework sequences within the variable regions of the heavy and light chain genes. Both of these approaches have, in fact, resulted in Mabs with lower immunogenicity. For example, the LL2 antibody has been humanized with retention of its native ability to bind antigen and become internalized, as disclosed in copending application Ser. No. 08/289,576, which is incorporated herein by reference in its entirety.

Mab engineering techniques have been used to produce another class of antibody molecule, namely the single chain antibody, scF$_v$. This molecule is produced by cloning the V$_H$ and V$_L$ segments from the Mab of interest and splicing them together with a short linker region interposed between them. These molecules, after proper design and renaturation, retain the antigen binding activity of the parent Mab and can be expressed at high levels in *E. coli*-based expression systems. These constructs then can provide a platform for the engineering of bifunctional single chain molecules that can link a second antigenic target to the first to retarget effector cells or molecules.

The invention utilizes pretargeting of the antigenic target with the fusion protein comprising the Mab or Fc fragments connected to a region of IL-15Rα. In this approach, enhanced tumor/normal tissue ratios of the Mab or Fc fragment are achieved by giving the nontoxic first reagent that has reactivity to the antigenic target. This is followed by a tumor targeting/washout interval that allows for uptake by tumor masses of this first agent and its clearance from normal tissues, after which the toxic conjugate is given.

Prior to the pretargeting with the fusion protein containing the region of IL-15α, the cells may be pretargeted with streptavidin-conjugated antibodies or biotinylated antibodies in conjunction with avidin and biotin. For example, biotinylated anti-CD20 antibodies can be administered, followed by administration of avidin to provide additional binding sites. Subsequently administered biotinylated IL-15Rα then attaches to the avidin sites.

Both two-step and three-step methods that utilize avidin-biotin chemistry can be employed. These generally involve, depending on the specific protocol, the administration of either avidin- or biotin-conjugated-mAb. This is followed, after an interval of 1–3 days, by the injection of biotin or avidin that is labeled with either a gamma-emitting radionuclide for imaging or by a beta or alpha emitter for therapy. The three-step method interposes a clearing step between the pretargeting and targeting steps. This step promotes the clearance of circulating, residual pretargeting agent, thereby reducing this pool and subsequent access to it by the targeting agent. In this system avidin is given to promote clearance since its elimination kinetics show a very rapid initial phase with a $t_{1/2}$=1 min which accounts for the majority of the total and a second phase with a $t_{1/2}$≈30 min.

The methods that use biotin and avidin lead to an increased number of sites for binding of active conjugate, but these improvements are mitigated by the fact that both avidin and the alternate protein, streptavidin, are immunogenic. Somewhat less than 30% of patients develop antibodies to avidin and a full 70% of patients develop antibodies to streptavidin. Accordingly, it is less preferable to use a pretargeting with biotin/avidin.

In a preferred embodiment according to the invention, therefore, a two-step procedure is used in which only the fusion protein containing the region of IL-15α fusion protein, in its optimal humanized form, is used to pretarget the malignant cells. The fusion protein according to the present invention has low immunogenic potential. The pretargeting agent bears human IL-15Rα, which has a high affinity for ligand. This fusion protein, owing to its relatively low molecular weight (70 kDa vs. 150 kDa for intact IgG), has the potential for greater penetration into the interior of tumors.

The second step reagent, the IL-15 construct, likewise has low immunogenic potential and a low molecular weight (rIL-15 from *E. coli* has a MW of 13 kDa) to aid in both tumor penetration and clearance from non-tumor sites. It is administered after the pretargeting, IL-15Rα fusion protein has localized on the malignant cells and substantially cleared from the circulation. This system could also be adapted to include a third step if this were necessary, i.e., an intervening preclearance. This can be done by galactosylating the IL-15 ligand. For higher galactose substitution IL-15 can be crosslinked covalently to asialofetuin.

The IL-15 ligand can be armed with a radionuclide or a toxin. The radionuclide can be either a diagnostic or therapeutic radionuclide. In a preferred embodiment, the IL-15 ligand is used to administer both radionuclide and toxin. The same IL-15 ligand can be armed with both radionuclide and toxin, or separate IL-15 ligands can be armed with radionuclide and toxin. Where separate IL-15 ligands armed with radionuclide and toxin are used, these may be administered together or sequentially.

When the IL-15 ligand is armed with a toxin, a preferred toxin is a ribonuclease, such as onconase. Onconase is a non-mammalian RNAse purified from *Rana pipiens* oocytes. It has been shown in clinical trials to have anti-tumor activity against human pancreatic cancer, but has been found to have minimal anti-tumor activity against B-cell malignancies such as B-cell lymphocytic leukemia.

The fusion protein and armed ligand conjugate are administered in a composition with a pharmaceutically acceptable carrier. In this regard, a pharmaceutically acceptable carrier is a material that can be used as a vehicle for administering the fusion protein or armed ligand because the material is inert or otherwise medically acceptable, as well as compatible with the fusion protein or armed ligand.

Various changes and modifications within the spirit and scope of the invention will become apparent to those skilled in the art from this detailed description. For example, since the $\beta/\gamma_c$ chains of IL-15 receptor are the same as the $\beta/\gamma_c$ chains of IL-2 receptor, the fusion protein can be used to introduce IL-2Rα onto the malignant cells, followed by administration of an RNase-IL-2 conjugate. Moreover, fusion proteins of either IL-15Rα or IL-2Rα can be made in which the fusion partner is an antibody other than an anti-CD20 antibody. This enables pretargeting of any tumor that carries a specific marker. Many antibodies and antibody fragments which specifically bind markers produced by or associated with tumors or infectious lesions have been disclosed, inter alia, in Hansen et al. U.S. Pat. No. 3,927,193 and Goldenberg U.S. Pat. Nos. 4,331,647, 4,348,376, 4,361,544, 4,468,457, 4,444,744, 4,460,459 and 4,460,561. Where the tumor additionally contains the $\beta/\gamma_c$ chains of IL-15/IL-2 receptors, the fusion protein will be rapidly internalized.

The following examples are illustrative of the present invention, but are not to be construed as limiting.

EXAMPLE 1

Determining of Expression of the $\beta/\gamma_c$ Chains of IL-2/IL-15 by a Malignant Cell Type Five B-lymphoma cell lines were assayed for IL-15 and IL-2 binding, along with two non-B cell lines (MLA 144, a T cell line known to express IL-2R$\beta/\gamma_c$ and MB-02, an AML derived cell line). $^{125}$I-labeled rIL-15 was used. Cold ligand inhibition was done with both IL-2 and IL-15 to allow estimation of the contribution of IL-15Rα to the overall binding.

Washed cells ($2\times10^6$) were suspended in binding buffer (growth medium). To these tubes was added either buffer or a 150-fold molar excess of cold rIL-15 or a 500-fold excess of cold rIL-2 for 15 min@4° C. Then $^{125}$I-IL-15 was added at 1.5 nM final concentration. Binding was allowed to proceed for 90 min@4° C. after which cells were transferred to 0.4 ml tubes and spun through a cushion of 80/20 dibutyl phthalate/olive oil. The tips were then cut off and counted in a gamma counter. The results are shown in Table 1.

TABLE 1

| CELL LINE | CPM $^{125}$I-IL-15 BOUND PER $2 \times 10^6$ CELLS WITH NO ADDITION - NONSPECIFIC | CPM $^{125}$I-IL-15 BOUND PER $2 \times 10^6$ CELLS + $500 \times$ EXCESS rIL-2 - NONSPEC. |
|---|---|---|
| MLA 144 | 708 | 310 |
| MB-02 | 502 | 448 |
| DHL-6 | 69 | 0 |
| DAUDI | 105 | 48 |
| RAJI | 634 | 303 |
| RAMOS | 48 | 19 |
| RL | 371 | 117 |

All the B-lymphoma lines tested showed a low but consistent specific binding of labeled IL-15, that was inhibited by cold IL-15. IL-2 competes with IL-15 for binding to IL-2Rβ/γ$_c$, but not with IL-15 binding to IL-15Rα. Similar degrees of inhibition by both unlabeled ligands suggest a preponderance of the β and γ chains over IL-15Rα, i.e., most of the binding in the cells was through the IL-2β/γ$_c$ dimer. Estimates based on cpm bound under saturating conditions along with degrees of iodine substitution derived from specific activity measurements showed that IL-15 receptor numbers on these cells was in the range of 50–500 sites/cell. This is similar in amount to the number of IL-2Rβ/γ$_c$ sites that has previously been observed on B-CLL and NHL cells. The presence of β/γ, even in low numbers, allows for the possibility of a continuously internalizing receptor system that can be bridged to cell marker antigen by way of a bispecific fusion protein and cognate ligand.

EXAMPLE 2

Assessment of Toxins for Effectiveness Against B-cell Malignancies

Three different mAbs, LL1, a class II invariant chain, LL2, an anti-CD22 antibody, and 5E9, an anti-transferrin receptor antibody, were conjugated to two RNase superfamily toxins, onconase and EDN. The resulting conjugates were tested on a panel of cell lines that included three B-lymphoma cell lines, Daudi, Raji, CA-46, a breast cancer line, MDA-MB-231, and a human T cell line, HuT 102. The results showed that LL2-onconase had the lowest IC$_{50}$ values of all the conjugates tested. Toxicity of onconase-based immunotoxins on B lymphoma cell line, Daudi, was further demonstrated with conjugates of onconase and LL2. LL2 is an antibody to CD22, an efficiently internalizing antigen. Both whole IgG and Fab' conjugates were prepared and were found to inhibit this cell line in the subnanomolar range. The effect was shown to be dependent on the CD22 reactivity of the conjugate, since inhibitory effects are nearly eliminated by excess cold antibody.

EXAMPLE 3

Construction of a Soluble IL-15Rα-1F5scF$_v$ Fusion Protein

The hybridoma 1 F5, IgG$_{2a}$κ is available from the American Type Culture Collection in Rockville, Md. This hybridoma is used to produce mAb both by growth of the hybridoma in tissue culture and/or ascites with subsequent purification on protein A-agarose. It is cultured in RPMI 1640 supplemented with 2 mM L-glutamine and 50 μg/ml each of penicillin and streptomycin and 10% FCS.

For isolation of the V$_H$ and V$_L$ genes of 1F5, $3 \times 10^7$ cells are used for isolation of total RNA. This is done by solubilizing washed cell pellets in Trizol reagent (Gibco/BRL, Grand Island, N.Y.) followed by RNA isolation via the acid-guanidium phenol-chloroform method. Five μg of total RNA are used as template for production of 1$^{st}$ strand cDNA using the AMV reverse transcriptase-based kit of Boehringer-Mannheim (Indianapolis, Ind.). From 2 to 5% of the resulting reaction products is used as a template for PCR amplification of the V$_H$ and the V$_L$ genes.

Universal primers, as described by Orlandi et al. (1989), are used in the PCR reactions. These primers are VH1FOR and VH1BACK for V$_H$ and VK1FOR and VKBACK1 for the kappa V$_L$. Alternatively, primers described by Leung et al. (1993) used successfully in chimerization and humanization of the LL2 and MN14 mAbs are used. Standard PCR conditions with 0.5 μM primers, 1.5 U Taq polymerase, 0.25 mM dNTPs, 2 mM MgCl$_2$ in the routine TrisHCl/KCl/gelatin buffer are used. PCR is carried out for 30 cycles with an initial denaturation for 4 min at 92° C., with cycles consisting of annealing@50° C. for 45 seconds, polymerization at 72° C. for 45 seconds and subsequent denaturation at 94° C. for 30 seconds.

Aliquots of the PCR products are analyzed on an ethidium bromide-stained 2% agarose gel. Appropriate PCR-amplified fragments are isolated on a 2% low-melt agarose gel and stained with ethidium bromide. Fragments are excised, the gel piece is melted and digested with β-agarase and then precipitated with ethanol. Aliquots of the gel purified material are cloned into the TA cloning vector pCRII (Invitrogen, San Diego), transformed into the recA-strain, XL1Blue (Invitrogen) and sequenced by standard dideoxy methodology with $^{35}$S-labeled precursor.

The construct uses a linker that is effective in multiple single chain F$_v$ antibodies (scF$_v$), the amino acid sequence (GGGGS)$_3$ to which is added three amino acids from the light chain elbow region to improve solubility and stabilize the monomeric form of the F$_v$. After inspecting the V$_H$ and V$_L$ sequences for restriction sites, oligonucleotides with an EcoRI, or appropriate alternate enzyme, overhang spanning the requisite 54 bp of the linker sequence are synthesized and allowed to anneal. This oligonucleotide is then ligated to the EcoRI-excised and gel-purified V$_H$ fragment by T4 DNA ligase. The V$_L$ fragment is excised and purified in the same fashion and then ligated to the V$_H$-linker fragment.

The 1F5scF$_v$ is religated into PCRII plasmid and transformed into bacteria and sequenced. The validated scf$_v$ sequence is ligated to an extracellular region of IL-15Rα. After the sequence is verified, the two binding regions of the fusion molecule are tested in binding assays. For situations where the F$_v$ moiety does not have adequate antigen binding activity, an additional F$_v$ is designed with the V$_L$ situated 5' to the V$_H$ with the same linker sequence.

PCR primers are selected based on the published nucleotide sequence of hIL-15Rα, starting at the NH$_2$-terminus of the mature protein on one strand and delimited on the opposite strand by the immediate extracellular juxtamembrane region, excluding the transmembrane and intracytoplasmic regions. The primers include adapter sequences to allow for sequential restriction digestion with EcoRI and NcoI for compatibility with the bacterial expression vector. RT-PCR amplification of IL-15Rα is carried out on total RNA from a cell line with high expression of IL-15Rα, such as HuT 102B2. Correct size fragments are cloned into the pCRII plasmid and sequenced, as described above. Sequence-validated fragments are then digested with EcoRI plus NcoI and ligated to the 1F5scF$_v$ fragment. The resulting orientation is shown below.

sIL-15Rα-V$_H$-GGGGSQPK(GGGGS)$_2$-V$_L$

The juxtamembrane region of sIL-15Rα is selected as a linker since, by analogy to IL-2Rα, the IL-15 binding region is predicted to be near the $NH_2$-terminus. In addition, several truncated forms of IL-15Rα have been shown to bind IL-15 as well as the full length, wild-type form. In order to obtain optimal binding, truncations of the sequence are tested.

The fusion sequence then is ligated into the pET21d vector (Novagen, Madison, Wis.) and transformed into the XL1Blue host. Bacterial clones are picked and sequenced using T7 and Sp6 primers in combination with internal specific primers. Clones with authentic sequences are expanded, and plasmids are isolated and transformed into the AD494(DE3) *E. coli* expression host. This host strain carries mutations in the thioredoxin reductase gene, thereby creating relatively oxidizing conditions that promote disulfide bond formation (Novagen).

EXAMPLE 4

Expression of sIL-15Rα-1F5scF$_v$ Fusion Protein

Transformed colonies are picked and expanded in LB broth to an $OD_{600}$≈0.5. They then are induced to express protein with 0.4 mM IPTG for 3 to 6 hours at 37° C. Bacterial cells from a small scale culture are pelleted and lysed with SDS-PAGE sample buffer, the debris is removed by centrifugation and an aliquot is loaded on a 10% SDS-PAGE gel. Part of the gel is cut off and stained with Coomassie Blue and the remainder is transblotted to an Immobilon-P membrane. This membrane then is stained with either a nickel-alkaline phosphatase conjugate (Qiagen, Chatsworth, Calif.), which recognizes the hexahistidine tag, or goat-anti-mouse-alkaline phosphatase (Kirkegaard and Perry, Gaithersburg, Md.), to detect immunoglobulin sequences. The blot is developed with the ECL substrate, CSPD, and exposed to photographic film.

Once good production is confirmed, expression cultures are scaled up. Initial scale-up is to cultures of ~1 liter. Bacterial cells are pelleted and washed in 300 mM NaCl/50 mM TrisHCl, pH=8.0, then resuspended in the same buffer and treated with 0.5 mg/ml lysozyme for 20 minutes on ice. The suspension is then sonicated on ice with three 30 second bursts. The insoluble material then is pelleted at 14,000× g for 5 minutes. The inclusion-body containing pellet is washed once with 50 mM TrisHCl, pH=8.0/200 mM NaCl/0.2% Triton X-100.

Solubilization and renaturation are performed according to an adapted version of the method of Kurucz et al. (1995), used with a bispecific scF$_v$ that is a fusion of two individual scF$_v$s. Briefly, the washed inclusion body preparation is solubilized with a buffer containing 2% sodium lauroylsarcosine/50 mM TrisHCl, pH=9.0 at a protein concentration of ~2 mg wet weight/ml. $CuSO_4$ is added at 50 μM and the mixture is allowed to oxidize in air at room temperature for 24 hours. Insoluble material is pelleted and the material is absorbed in batch mode to $Ni^{2+}$-IDA resin (Talon™, Clontech, Palo Alto, Calif.) for 20 minutes at room temperature, based on the binding capacity of the resin.

Total protein concentrations is determined by a modified Bradford assay (Coomassie Plus™, Pierce, Rockford, Ill.) in the low level mode with buffer blanks. In the case of detergent interference, a detergent insensitive assay using bicinchoninic acid is used. With this detergent, $A_{280}$ estimates can be made. After adsorption the resin is transferred to a column and washed with 20 column volumes of the solubilizing buffer followed by ≧20 column volumes, or until $A_{280}$<0.02, with 8M urea/50 mM MES, pH=6.0. Bound product is eluted in 8M urea/300 mM imidazole/TrisHCl, pH=7.4. All fractions are saved and analyzed by SDS-PAGE with Coomassie staining. Fractions of sufficient purity then are dialyzed versus 0.4 M arginine/50 μM $CuSo_4$/50 mM TrisHCl, pH=8.0.

EXAMPLE 5

Assay of Antigen Binding Activity of sIL-15Rα-1F5scF$_v$ Fusion Protein

Antigen binding activity of the fusion protein is assayed by radiolabeling it with $^{125}$ I by the Iodogen method such that specific activity does not exceed 20 μCi/μg. Panels of human cell lines that are known to be positive or negative for CD20 are tested in a standard binding assay in the presence and absence of cold 1F5, cold fusion protein and cold IL-15. Binding occurs through the anti-CD20 moiety. After 1 hour on ice the cells are spun through a cushion of 80/20, dibutyl phthalate/olive oil and the tips of the tubes are cut off and counted in a gamma counter.

To test for IL-15 binding capacity a cell binding assays is used. A B-cell line with the high expression of CD20 is used. Cold receptor-F$_v$ fusion protein is allowed to bind for 40 minutes on ice. Cells are washed twice and $^{125}$I-IL-15 are added. IL-15 labeled by the Iodogen method to specific activities of up to 70 μCi/μg is added at 1 nM in the presence of a 200-fold molar excess of cold IL-15 and cold IL-2 as a negative control (IL-2 does not bind to IL-15Rα). After another 40 minutes on ice, the cells are spun through an oil cushion and counted as above.

EXAMPLE 6

Assay of Ability of sIL-15Rα-1F5scF$_v$ Fusion Protein to Internalize CD20

The fusion protein and parental 1F5 are labeled in parallel with $^{125}$I. The CD20+ cell line, RL, is used. Binding is carried out on ice at 5 nM for both labels on equal aliquots of cells. Cold IL-15 or cold IL-2 is added to some tubes to assess the effects on internalization. Unbound labels are removed by pelleting and washing the cells. A $t_0$ value is determined and the remaining aliquots are placed at 37° C. and removed at various time intervals. Catabolized and released $^{125}$I is distinguished from dissociated, intact protein label by precipitation with 10% TCA. If enhanced internalization occurs when cold IL-15 is added to labeled fusion protein and not to controls, a reverse experiment using labeled IL-15 and unlabeled fusion protein is done to approximate the in vivo situation.

In vitro studies using the residualizing labels $^{88}$Y, $^{111}$In, $^{125}$I-dilactitol-tyramine also are done. These agents better represent the behavior of the radionuclides to be tested for therapy, namely, $^{90}$Y and $^{131}$I on a residualizing label. For Y and In radiometals IL-15 is reacted with isothiocyanotobenzyl-DTPA and then tested for retention of bindability in a cold ligand inhibition assay as described above, following protocols for chelate labeling. Briefly, rIL-15 is dialyzed against 0.1 M Hepes, pH=8.2. To this is added a 6-fold molar excess of isothiocyanotobenzyl-DTPA. The reaction is carried out for 2 hours at room temperature. Labeled IL-15 is separated from unbound chelate by gel filtration on a PD-10 column. If adequate bioactivity is retained, the chelated IL-15 is dialyzed into 0.1 M sodium acetate, pH=6.0 under metal-free conditions in preparation for loading with radiometal.

EXAMPLE 7

Construction of a IL-15/Onconase Immunotoxin

A fusion protein consisting of IL-15 and onconase is genetically engineered following procedures outlined by Rybak (1995) for the production of mAb-onconase fusion proteins. Briefly, a sequence-confirmed fragment corresponding to the mature IL-15 protein is ligated to the sequence of onconase with the IL-15 sequence lying 5', though the other orientation also can be evaluated. Onconase genes are cloned from two or more frog species. Authentic fragments representing the fusion sequence are subcloned into the pET21d vector again using a C-terminal hexahistidine tag. The complete sequence encoding the entire IL-15-onconase fusion protein is confirmed in the pET vector in the XL1Blue strain as above. Appropriate clones are expanded to produce plasmid for transformation of the AD494 (DE3) E. coli expression strain.

Transformed clones are picked and grown in small scale culture, induced with IPTG, lysed in SDS sample buffer and run out on a SDS-PAGE gel for Coomassie staining and transblotting for detection both with anti-IL15 antibodies and anti-onconase antibodies. Isolation and washing of inclusion bodies, their solubilization, renaturation and subsequent purification are performed using the steps outlined above. The final product is tested for its ability to bind the IL-15 receptor by labeling with $^{125}$I and comparing it with equimolar concentrations of similarly labeled IL-15 in the cell binding assay described above.

Conjugates that retains bindability are tested for cytotoxicity on cell lines known to express receptors for IL-15, such as HuT 102B2 or MLA144. A $^3$H-leucine incorporation assay is performed in which 1×10$^4$ HuT 102B2 or MLA144 cells are plated in duplicate wells in a 96-well plate and cultured in the presence or absence of IL-2, IL-15, IL-15-onconase and media alone for 30 hours, at which point label is added.

Specificity is checked by adding IL-2 or IL-15 together with the fusion protein to look for inhibition of cytotoxicity. IL-15 should efficiently inhibit, while IL-2 should inhibit only partially. After a 6 hour incorporation period, proteins are harvested onto a type B glass fiber filter mat and counted in a MicroBeta scintillation counter (Wallac, Gaithersburg, Md.).

The assay is repeated for cytotoxic fusion protein with a model NHL cell line such as RL. In this case the assay is carried out in the presence and absence of the sIL-15Rα-1F5scF$_v$ fusion protein to determine toxicity and the ability to bind and internalize greater amounts of the immunotoxin. A dose response curve for each experimental and control condition is generated. To control for nonspecific toxicity a CD20-cell line us used. Inhibition of toxicity by the addition of excess unlabeled 1F5 mAb, IL-15 and IL-2 also is tested.

EXAMPLE 8

Antibody-onconase Conjugates

In order to assess the cytotoxic activity of onconase-based immunotoxins on B lymphoma cell lines, LL2-onconase conjugates were prepared, and their effects tested on Daudi, B-lymphoma cell line. Both whole IgG and Fab' conjugates were prepared and were found to inhibit this cell line in the subnanomolar range. Furthermore, the effect was shown to be dependent on the CD22 reactivity of the conjugate since inhibitory effects were nearly eliminated by excess cold antibody.

In another series of experiments different permutations of conjugates between three mAbs (LL1 [class II invariant chain], LL2 and 5E9[anti-transferrin receptor]) and two RNase superfamily toxins (onconase and EDN) were tested on a panel of cell lines that included three B-lymphoma cell lines (Daudi, Raji, CA-46), MDA-MB-231, a breast cancer line, and HuT 102, a human T cell line. Dose response curves were done with the readout being protein synthesis as assessed by $^3$H-leucine incorporation. Cells were plated in the presence of an absence of mAb, toxin or conjugate, cultured for 16 hours and then pulsed with 1 μCi/well of label. Incorporation was measured by harvesting the cells onto a type B glass fiber filter, followed by scintillation counting. As shown in Table 2, LL2-onconase had the lowest IC$_{50}$ values of all the conjugates tested.

TABLE 2

Cytotoxicity of Onconase and EDN conjugates vs. Component Proteins IC$_{50}$(pM)

| Cell line | LL2-Onc | LL1-Onc | Onc | LL2 | LL2-EDN | 5E9-EDN | EDN |
|---|---|---|---|---|---|---|---|
| Daudi | 100 | | >200,000 | >23000 | >43000 | | |
| CA-46 | 800 | 2300 | >200,000 | >23000 | >43000 | | |
| Raji | 800 | | >200,000 | >23000 | | | |

TABLE 2-continued

Cytotoxicity of Onconase and EDN conjugates vs. Component Proteins IC$_{50}$(pM)

| Cell line | LL2-Onc | LL1-Onc | Onc | LL2 | LL2-EDN | 5E9-EDN | EDN |
|---|---|---|---|---|---|---|---|
| Hut-102 | >40,000 | | 37,000 | | | | |
| MDA-MB-0231 | | | | | | 1600 | >7,000,000 |

EXAMPLE 9

Therapy of B-CLL

A patient having B-CLL is infused intraveneously with a sterile, pyrogen-free solution containing a target dose of sIL-15Rα-1F5scF$_v$ fusion protein labeled with I$^{123}$ in phosphate-buffered saline (PBS), prepared according to Examples 3 and 4. After the fusion protein has bound to malignant B cells and has substantially cleared from the circulation of the patient, as monitored by gamma camera imaging, the patient then is infused intravenously with a sterile, pyrogen-free PBS solution that contains a therapeutic dose of IL-15/onconase immunotoxin conjugate, prepared according to Example 7. Subsequent radioimmunodetection, with labeled anti-CD20 shows significant reduction in the lymphoma.

What is claimed is:

1. A conjugate of a non-immunogenic RNase and a cell-specific cytokine, wherein said conjugate is a fusion protein.

2. A conjugate as claimed in claim 1, wherein said RNase is a frog RNAse.

3. A conjugate as claimed in claim 1, wherein said cytokine is IL-15.

4. A conjugate as claimed in claim 1, wherein said RNase is onconase.

5. A conjugate as claimed in claim 4, which additionally comprises a diagnostic radionuclide.

6. A composition comprising a conjugate according to claim 1, and a pharmaceutically acceptable carrier.

7. A composition as claimed in claim 6, additionally comprising a diagnostic radionuclide conjugated to said cytokine.

* * * * *